United States Patent
Omrane (10) Patent No.: US 10,279,064 B2
(45) Date of Patent: May 7, 2019

(54) LOW VOLTAGE ELECTRON BEAM DOSIMETER DEVICE AND METHOD

(71) Applicant: Tetra Laval Holdings & Finance S.A., Pully (CH)

(72) Inventor: Alaa Omrane, Lund (SE)

(73) Assignee: Tetra Laval Holdings & Finance S.A., Pully (CH)

( * ) Notice: Subject to any disclaimer, the term of this patent is extended or adjusted under 35 U.S.C. 154(b) by 26 days.

(21) Appl. No.: 15/527,490

(22) PCT Filed: Nov. 16, 2015

(86) PCT No.: PCT/EP2015/076638
§ 371 (c)(1),
(2) Date: May 17, 2017

(87) PCT Pub. No.: WO2016/079032
PCT Pub. Date: May 26, 2016

(65) Prior Publication Data
US 2017/0319729 A1    Nov. 9, 2017

(30) Foreign Application Priority Data
Nov. 18, 2014  (SE) .................................. 1451383

(51) Int. Cl.
*A61L 2/28* (2006.01)
*A61L 2/08* (2006.01)
(Continued)

(52) U.S. Cl.
CPC .................. *A61L 2/28* (2013.01); *A61L 2/087* (2013.01); *B65B 55/08* (2013.01); *G01T 1/29* (2013.01);
(Continued)

(58) Field of Classification Search
CPC ............ A61L 2/28; A61L 2/087; B65B 55/08
See application file for complete search history.

(56) References Cited

U.S. PATENT DOCUMENTS 5,399,868 A   3/1995  Jones et al.
6,617,596 B1  9/2003  Korenev
(Continued)

FOREIGN PATENT DOCUMENTS

CN    203169652 U    9/2013
EP    0 560 627 A2   9/1993
(Continued)

OTHER PUBLICATIONS

Feng, et al. "Influence of surface charge on the cathodoluminescence of Ce:Yag" *Journal of Applied Phsyics* 73(8): 3926-3931 (1993).
(Continued)

*Primary Examiner* — Michael C Bryant
(74) *Attorney, Agent, or Firm* — Knobbe, Martens, Olson & Bear LLP (57) ABSTRACT

In some embodiments, a sensor assembly for continuous measurement of at least one dose control parameter of an electron beam during a substantial part of the duration of a sterilizing process of package material includes an electron beam emitter adapted to emit electron beam (e–) from an electron exit window and a sensor device that includes: a sensor surface having an electron excitable material arranged to be radiated with at least a part of said electron beam (e–), so as to excite said electron excitable material so that said electron excitable material emits luminescence and a detector arranged and adapted to detect said luminescence. The electron beam emitter is adapted to emit a continuous electron beam (e–) during a predetermined time period so as to irradiate and sterilize package material.

20 Claims, 4 Drawing Sheets

(51) Int. Cl.
  *B65B 55/08* (2006.01)
  *G01T 1/29* (2006.01)
  *H01J 37/244* (2006.01)
  *H01J 37/304* (2006.01)
(52) U.S. Cl.
  CPC .......... *H01J 37/244* (2013.01); *H01J 37/304* (2013.01); *A61L 2202/14* (2013.01); *A61L 2202/23* (2013.01)

(56) References Cited

U.S. PATENT DOCUMENTS

| | | | |
|---|---|---|---|
| 2004/0084631 A1 | 5/2004 | Spoonhower et al. | |
| 2007/0290148 A1 | 12/2007 | Kristiansson et al. | |
| 2011/0006225 A1* | 1/2011 | Fletcher | A61L 2/087 250/492.3 |
| 2011/0012032 A1* | 1/2011 | Bufano | A61L 2/087 250/492.3 |
| 2011/0198513 A1 | 8/2011 | Holm | |
| 2013/0252340 A1* | 9/2013 | Haertling | A61L 2/087 436/1 |
| 2014/0117259 A1 | 5/2014 | Holm et al. | |
| 2014/0299786 A1 | 10/2014 | Yokobayashi et al. | |
| 2015/0083923 A1 | 3/2015 | Stanton et al. | |
| 2016/0361449 A1* | 12/2016 | Omrane | A61L 2/087 |

FOREIGN PATENT DOCUMENTS

| | | |
|---|---|---|
| EP | 1 416 294 A1 | 5/2004 |
| EP | 2 371 397 | 10/2011 |
| EP | 2 755 052 A1 | 7/2014 |
| EP | 2 769 922 A1 | 8/2014 |
| WO | WO 02/061464 A1 | 8/2002 |
| WO | WO 2005/002973 | 1/2005 |
| WO | WO 2007/050007 | 5/2007 |
| WO | WO 2007/145560 A1 | 12/2007 |
| WO | WO 2011/011079 | 1/2011 |
| WO | WO 2012/097770 A1 | 7/2012 |
| WO | WO 2013/004565 A1 | 1/2013 |
| WO | WO 2013/184204 A2 | 12/2013 |
| WO | WO2014/086674 | 6/2014 |
| WO | WO 2014/086675 A2 | 6/2014 |
| WO | WO 2014/095838 A1 | 6/2014 |

OTHER PUBLICATIONS

International Search Report and Written Opinion for PCT/EP2015/076638 dated Jan. 20, 2016 in 12 pages.
International-type Search Report for Swedish App. No. 1451383-2 dated Apr. 6, 2015 in 6 pages.

* cited by examiner

LOW VOLTAGE ELECTRON BEAM DOSIMETER DEVICE AND METHOD

TECHNICAL FIELD

The present invention relates to sensor device suitable for use as a dosimeter for a low voltage electron beam emitter used for sterilizing purposes.

BACKGROUND OF THE INVENTION

Within the food industry, it is common practice to pack liquid and partly liquid food products in packaging containers manufactured from a packaging laminate comprising a core layer of paper or paperboard and one or more barrier layers of, for example, polymer material or aluminium foil.

An increasingly common packaging type is the "carton bottle" manufactured in a filling machine in that packaging blanks of the above-described packaging laminate are formed and sealed as a sleeve. Said sleeve is closed in one end in that a top of thermoplastic material is injection moulded directly on the sleeve end portion. The sheets of packaging laminate may be cut from a magazine reel of packaging laminate.

When the top is finished the packaging container is ready to be filled with product through the still open bottom, and then sealed and finally folded. Before the filling operation the packaging container undergoes treatment. If distribution and storage is to be made in chilled temperature the packaging container is disinfected, whereas if distribution and storage is to be made in ambient temperature, the packaging container needs to be sterilized. A conventional way of sterilizing a ready-to-fill packaging container is to use hydrogen peroxide, preferably in gas phase.

Another way to sterilize such packaging containers is to irradiate it by means of a low voltage electron beam emitted from an electron beam emitter. An example of linear irradiation by electron beam of ready-to-fill packaging containers is disclosed in the international patent publication WO 2005/002973. The electron beam emitter is cylindrical with an electron exit window positioned at one of the distal ends. The packaging container is lifted to surround the electron beam emitter during the sterilization cycle. Other examples of irradiation of packaging containers, in these cases PET bottles, are described in for example WO 2011/011079 and EP 2 371 397, the latter describing a rotary system. In these systems emitters are used having a diameter small enough to be passed through a neck portion of the bottles.

In order to monitor correct operation of the electron beam emitters, and thereby being able to secure sterility assurance level, it is common practise to perform dosimetry tests. These tests are made regularly, generally daily, throughout the lifetime of the electron beam emitter. In general, dosimetry tests involve adding a dosimeter means, i.e. a patch reacting on radiation exposure, to a packaging container to measure if a correct absorbed dose is obtained during radiation. At the same time measurements of voltage and current are made in the electron beam emitter. The current over the filament is measured. By comparing the current fed to the filament and current leaving the filament it is possible to determine the amount of electrons emitted from the filament. In addition, the voltage, i.e. the electric potential, between the electron exit window and the filament is measured. The measured value of voltage and current is then used as a set value during production of packaging containers. The current and voltage are continuously monitored during production, and as long as the value is not lower than the set value it is assumed that the packaging containers receive the correct dose.

However, the use of disposable dosimeter patches or dosimeter films requires a lot of manual work for performing the dosimeter measurements. The dosimeter films also have to be processed in a laboratory for obtaining the dosimeter values. The dosimeter films further cannot stand for high temperatures, limiting the measurement duration. There is thus a need for an automated dosimeter measurement. WO2007050007 and WO2014086674 suggest solutions using a dose measuring device having a conductor that is permanently or temporarily placed in front of the electron beam emitter window. The conductor is charged by the electron beam and a current that is proportional to the electron beam intensity may be measured and the dose may thus be calculated. These dose measuring devices will however produce a very coarse measurement of the electron beam profile since each conductor will correspond to a summarized line measurement along the extension of the conductor that is exposed to the electron beam. When placed permanently in front the window, they will present a barrier shadowing some part of the electron beam profile. Each conductor will also be heated by the electrons hitting it, presenting a risk of damaging the exit window of the electron beam emitter.

There is thus a need for an improved sensor device for dosimeter measurement for an electron beam emitter that has a resolution that is as good as or better than the resolution of a dosimeter film.

SUMMARY OF THE INVENTION

It is an object of the present invention to improve the current state of the art, to solve the problems of the prior art, and to provide an improved sensor device for measurement of at least one dose control parameter of an electron beam.

These and other objects are achieved by a sensor assembly for continuous measurement of at least one dose control parameter of an electron beam during a substantial part of the duration of a sterilizing process of package material, said sensor assembly comprising an electron beam emitter adapted to emit a electron beam from an electron exit window of said electron beam emitter; and a sensor device. The sensor device comprises a sensor surface comprising an electron excitable material arranged to be radiated with at least a part of said electron beam, so as to excite said electron excitable material so that said electron excitable material emits luminescence; and a detector arranged and adapted to detect said luminescence. Said electron beam emitter is further adapted to emit a continuous electron beam during a predetermined time period so as to irradiate and sterilize package material.

The luminescence from said electron excitable material is in the form of fluorescence or phosphorescence and is proportional to the intensity of the electron beam hitting the sensor surface of the electron excitable material. Each electron hitting the sensor surface will produce said luminescence in the spot where electrons hits the surface. The sensor surface and the electron excitable material are transparent to the induced luminescence. By placing a detector that can collect some of the emitted luminescence, i.e. said detector is looking at the electron excitable material, the intensity of the electron beam may be estimated and thereby also the dose of electrons emitted by the electron beam emitter. If using a 2D detector an image of the sensor surface may be recorded producing an image where the intensity in each pixel corresponds to the intensity of the electron beam inducing the emission in that pixel of the image.

The exited state of the excitable material is temporary with a lifetime in the range of a few nanoseconds to a few milliseconds, producing luminescence as the excitable material is de-excited. The material is thus not permanently affected by the electron beam and the sensor surface is thus reusable and may be used for continuous time resolved measurements of the electron beam profile intensity for an unlimited time period. The limit of the time resolved resolution is determined by said lifetime as long as the detector is fast enough.

The electron beam emitter is adapted to irradiate a package material with electrons during a predetermined time period that is long enough to kill all bacteria on the package material, thus sterilizing it. The sensor assembly is thus adapted to measure the entire duration of such a sterilizing process to monitor the dose control parameter during a substantial part of that duration.

When measuring the dose control parameter of the beam profile, it is desirable to perform the measurement when the electron beam emitter has been operating for a certain time period, since the beam profile intensity will change initially before it reaches a steady state. The steady state is the desired state to measure the beam profile in, as that is the normal operating state of the electron beam emitter in use for sterilizing purposes. Pulsing the electron beam emitter would produce a misleading results perhaps not corresponding to the real operating state of the beam emitter.

According to a preferred embodiment of the present invention the electron beam emitter is a low voltage electron beam emitter. The use of a low voltage beam emitter in the range of 20-800 keV, preferably 40-400 keV, more preferably 60-250 keV, most preferably 70-150 keV, allows the beam profile to be large. It also allows continuous measurement of the beam profile using the described sensor device with less heat problems as the heat produced in the sensor surface is proportional to the voltage of the electron beam emitter. A high voltage electron beam emitter may cause too much heat, damaging the sensor surface of the sensor device or other parts of the sensor device.

The excitable material of the sensor device may be e.g. a YAG:Ce crystal, a YAG:Ce powder, $CaF_2$:Eu, $Gd_2O_2S$:Tb, LuAG:Ce, YAP:Ce ($Mg_4FGeO_6$:Mn) or any other material excitable by electrons producing emission in a measurable frequency. In case of using a YAG:Ce scintillator crystal, the sensor surface is completely made of a clear plate of the crystal. The spatial resolution of measurements produced with such a clear crystal will be very high. However, also a phosphorescent powder of YAG:Ce or any of the materials listed above coated to a transparent plate will work, although the resolution will decrease somewhat due to the uneven surface of coated powder. YAG:Ce has a broadband luminescence around 530 nm with a full-width-half-maximum (FWHM) of approximately 95 nm.

The detector of the sensor device may be a CCD-camera, an ICCD-camera, a COMS-camera, a photo multiplier, a photo diode, or any other suitable sensor for detecting the induced luminescence emission. In case of using YAG:Ce as electron excitable material, the strong yellow emission around 530 nm allows the use of normal cameras, avoiding the need for expensive specialized detectors.

According to a further embodiment of the present invention the sensor assembly according to the invention further has a sensor surface on the sensor device that is covered by a metal coating facing the electron beam emitter. The metal coating will work as a mirror for the induced luminescence while allowing electrons to pass through it on their way towards the electron excitable material. The mirror metal coating will enhance the signal strength of the luminescence and will enhance the contrast for the detector as it will block most radiation in the visible spectrum originating from the side facing the electron emitter for the camera. Problems of background luminescence in the measurement will thus be heavily reduced. The mirror metal coating will e.g. provide protection for radiation originating from plasma caused by the electron emitter.

The metal coating may preferably be made a metal comprised in the group of: rhodium, zirconium, platinum, osmium, iridium, ruthenium, and palladium. The coating is preferably thin, with a thickness in the range of 20 nm-1 μm, preferably around 100 nm, so as to not absorb too much of the electron emission from the electron emitter. The materials from the platinum group metals are especially suitable as they withstand corrosion very well thus presenting the desired mirror effect for a long time without degradation or need of cleaning the surface from disturbing corrosion that may absorb electron emission. Rhodium is a preferred choice as it withstands corrosion well and is well suited for coating on the sensor surface.

The metal surface is preferably coated to the sensor surface using physical vapor deposition (PVD) to get a thin and evenly thick layer.

According to a further aspect of the present invention the coated metal surface on the sensor surface is grounded so as to lead away any electrical charges deposited on the metal coating. Electrical charges on the metal coating may otherwise disturb the measurements of the sensor device.

According to a still further aspect of the present invention the sensor device may comprise a glass window, e.g. a Sapphire window, arranged in thermal connection with the sensor surface, said window facing the detector and being in thermal connection with a further heat conductive element so as to conduct heat from said glass window and said sensor surface. This facilitates the possibility to increase the energy of the electron beam leading away heat induced in the sensor surface so that the sensor surface is not damaged by excessive heating.

According to a still further aspect of the present invention the sensor device may comprise a lead window arranged between the sensor surface and the detector. The lead window is thin to allow the induced luminescence from the electron excitable material to penetrate while blocking any X-ray emission produced by the electron beam emitter. This embodiment is especially good when the X-ray emission is strong enough to penetrate the barrier of the electron excitable material present for the X-ray emission.

According to a still further aspect of the present invention said detector is collecting the luminescence from said sensor surface via an optical fiber. The detector may in that case be placed remotely, making the lead window unnecessary if the detector is placed protected from X-ray radiation. The sensor surface, preferably made of a small window of YAG:Ce crystal, may have roughly the same diameter as the fiber and may be attached directly onto the fiber tip with or without the metal coating and the sapphire window. As an optical fiber does not lead X-ray radiation, the lead window is not as important in this embodiment. A very small detector for point measurements is thereby achieved using an optical fiber. If a 1D or 2D measurement is required, an array or matrix of the fiber detector may be bundled together.

The dose control parameter measured may be the dose rate (kGy/s) so that the output measurement result is comparable to traditional dosimetry equipment complying with industry standards for dose measurements.

It is further preferred that the sensor device is connected to processing means for processing the information from the sensor; and is arranged to generate a 1D or 2D image of the dose control parameter of the electron beam. The processing means may be adapted to calculate the dose rate from the time resolved intensity measurements of the induced luminescence from the electron excitable material. In case of a 1D detector, the total dose rate of the electron beam emitter may be measured and in case of a 2D detector a 2D image of the dose rate may be measured.

It is further preferable that the sensor surface is large enough to catch the entire cross section of the electron beam, so as to be able to measure and/or image the entire dose rate of the electron beam emitter.

The present invention further relates to packaging machine for producing food packages comprising the sensor device described above according to the present invention. Placing the sensor device in a packaging machine may allow for online measurements of the electron beam emitter or emitters, especially if the electron beam emitters are moving in the machine.

The present invention further relates to a method for continuous measurement of at least one dose control parameter of an electron beam of an electron beam emitter during a substantial part of the duration of a sterilizing process of package material, said method comprising the steps of forcing the electrons of an electron beam to hit a sensor surface, said sensor surface being adapted to generate luminescence when hit by the electrons (e−); and detecting the generated luminescence by at least one detector.

It should be noted that the inventive method may incorporate any of the features described above in association of the inventive device and has the same corresponding advantages.

DESCRIPTION OF THE DRAWINGS

In the following the present invention will be described in greater detail together with the accompanying drawings, in which.

DETAILED DESCRIPTION

Figure 1:
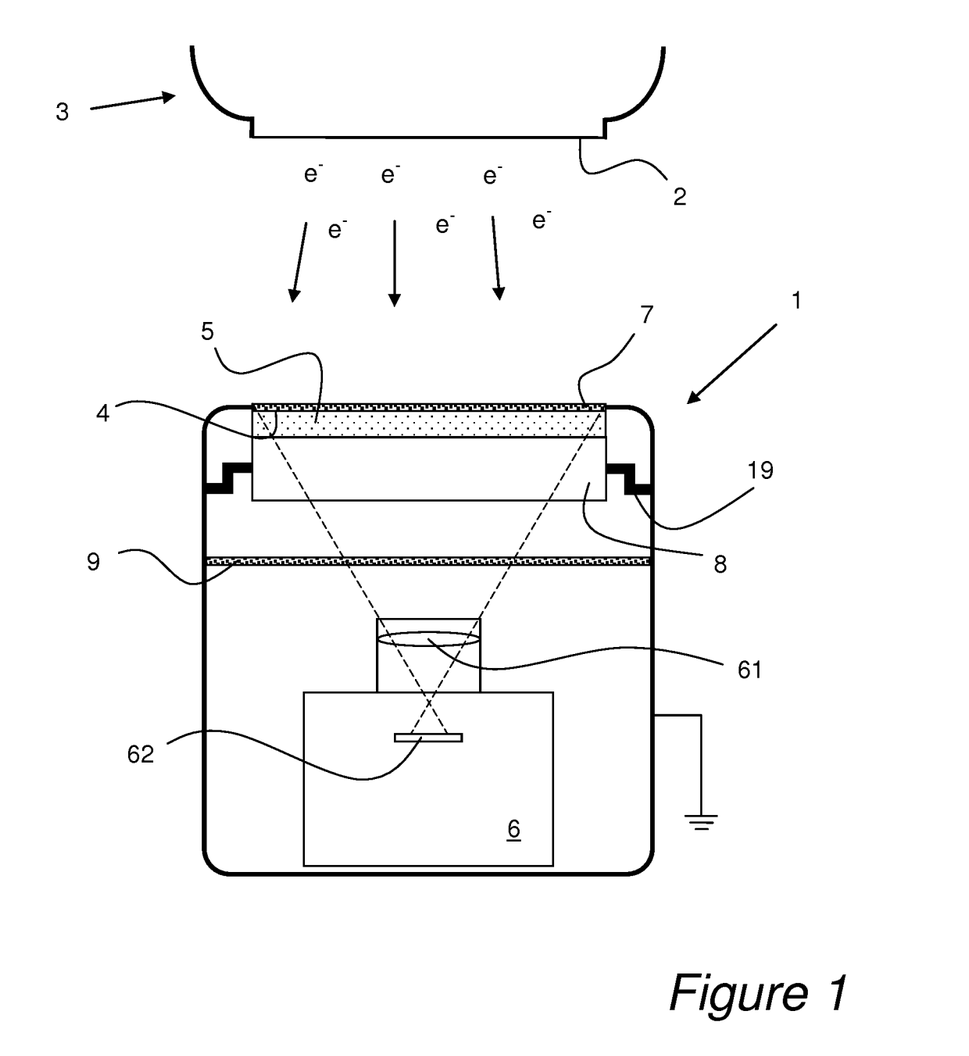
FIG. 1 shows a schematic view of the sensor assembly according to the invention.

FIG. 1 shows a schematic figure of the sensor assembly of the present invention. The electron emitter 3 is a low voltage electron beam emitter for sterilizing package material as e.g. the inside of a bottle or the surface of a package material sheet. The low voltage electron beam emitter is directed towards the sensor device 1 so that the entire electron beam (e−) hits the sensor surface 4 of the sensor device 1. The sensor surface 4 has an electron excitable material attached to it, e.g. a phosphor material, but the sensor surface 4 and the electron excitable material 5 may also be the same, formed from a scintillator crystal plate 5. In this embodiment the electron excitable material 5 is scintillator plate made of the YAG:Ce, having a broadband fluorescence around 530 nm (95 nm FWHM).

The sensor surface 4 is in FIG. 1 coated with a thin metal coating 7 made of Rhodium or Zirconium, about 100 nm thick. The metal coating 7 is arranged on the side facing the electron beam emitter 3. On the other side of the electron excitable material a lead window 9 and a sapphire window 8 are placed. The order of the latter windows 8, 9 may be reversed.

In FIG. 1, a detector 6 in form of a camera 6 is placed having a lens device 61 projecting an image of the sensor surface 5 (illustrated by the dashed lines) onto the camera sensor chip 62 of the camera. The lens device 61 is naturally only an illustration and could be any lens package suitable for the imaging of the sensor surface 4.

The electron excitable material 5 is excited by the electrons of the electron beam (e−) inducing luminescence in each position of the sensor surface 4. The induced luminescence is emitted in all directions from each point in the electron excitable material 5. The metal coating 7 works as a mirror for the induced luminescence, increasing the signal for the camera 6 by up to 100%. Also the contrast is increased as anything on the far side of the metal coating, as seen from the camera 6, is blocked by the metal coating 7.

The metal coating 7 is further grounded (in FIG. 1 via the housing of the sensor device 1) so as to lead away any charges deposited on the surface of the sensor device 1 where the electron beam (e−) hits the sensor device.

The sapphire window 8 has the function of leading off heat from the other layers 7, 5, 9 via heat pipes 19 to another heat conductive part of the sensor device, in FIG. 1, the housing of the sensor device 1 functioning as a heat sink. The sapphire window thus functions as a heat sink for the electron excitable material, the YAG:Ce scintillator crystal, so that the excess heat generated by the electron beam emitter may be conducted away from the YAG:Ce crystal. In that way it is possible to increase the energy of the electron beam without damaging the YAG:Ce scintillator crystal plate or any of the other layers attached to it.

The sapphire window 8 is preferably in direct contact with the electron excitable material 5, especially is the electron excitable material 5 is a scintillator plate to maximize thermal conduction from the sensor material 5.

The sensor material 5 may, if it is a phosphorescent powder, be coated directly onto the sapphire window.

When operating the electron beam emitter 3, X-ray emission will be generated that may disturb or damage the detector camera 6. The lead window 9 will however absorb any X-ray emission shielding the detector 6 from X-ray emission.

The low voltage electron beam emitter of FIG. 1 may be used e.g. in a packing machine where two LVEB emitters are placed facing each other having an unfolded carton sheet for packages being fed between the LVEB emitters for sterilization purposes. To ensure that the LVEB emitters emit the specified amount of electrons for the sterilization, the beam profile dose rate of the LVEB emitters will have to be regularly checked. The setup shown in FIG. 1 may be such a service check of the LVEB emitter, where the LVEB has been temporary removed from the packing machine for the dosimetry measurement.

Figure 2:
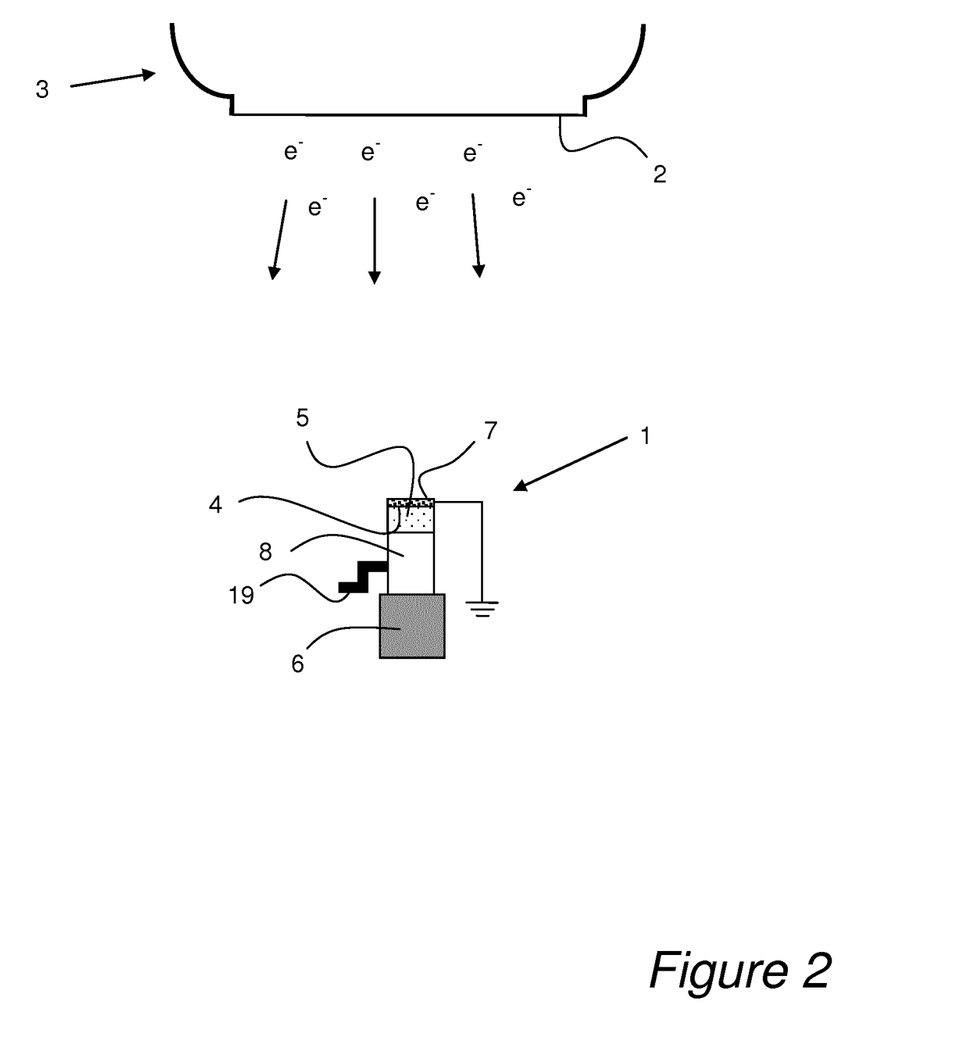
FIG. 2 shows a schematic view of a second embodiment of the sensor assembly according to the present invention with a simplified detector.

FIG. 2 shows a simplified detector assembly according to the present invention. The detector is a simple detector, e.g. a photo diode or photo multiplier tube. The other layers are directly attached to the detector 6. In FIG. 2, the lead window is omitted although it could also be included between the sapphire window 8 and the sensor surface 4. The sensor surface is also in this embodiment coated with a metal coating of preferably rhodium.

Figure 3:
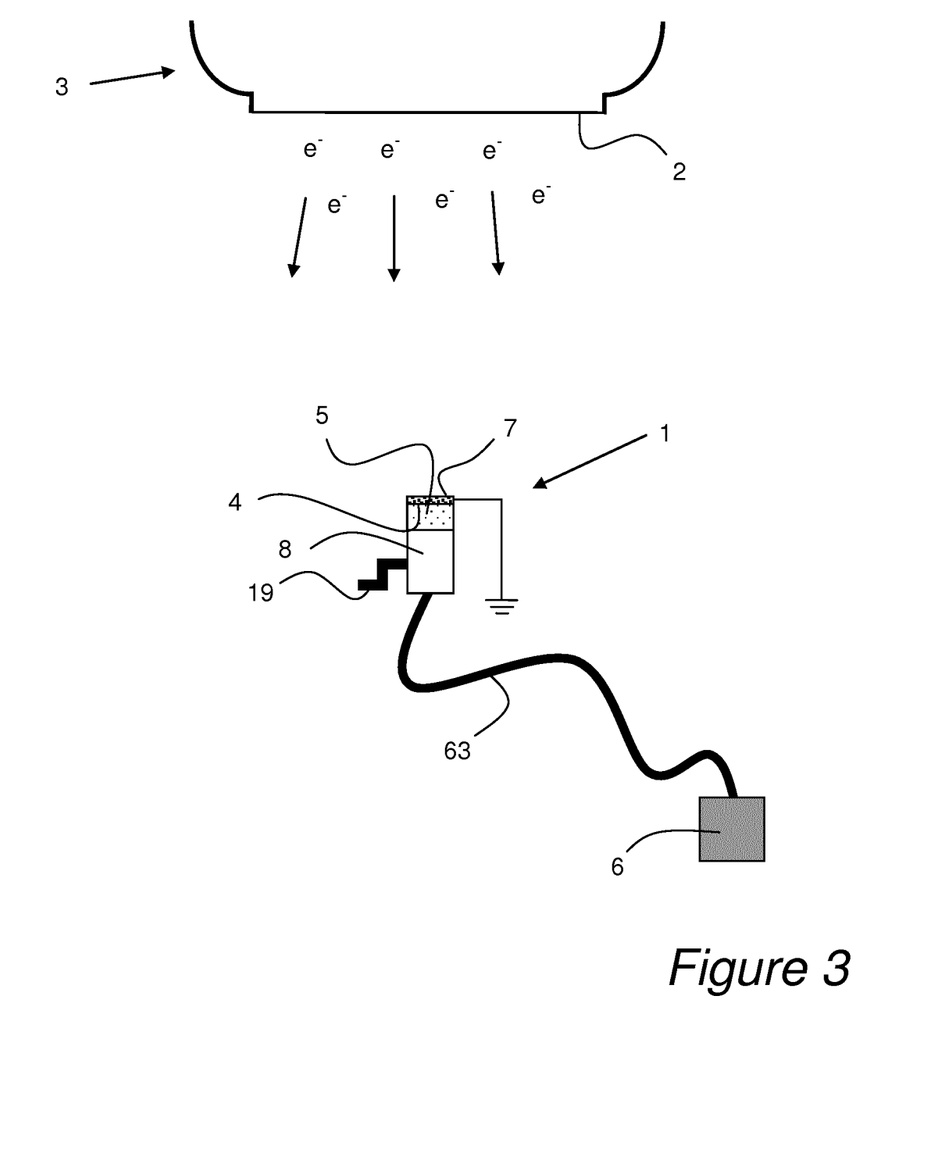
FIG. 3 shows a schematic view of a third embodiment of the sensor assembly according to the present invention with a simplified detector using optical fibers.

FIG. 3 shows a further embodiment of the present invention. The sensor assembly is a simplified detector as in FIG. 2, with the difference that the detector 6 is separated from the sensor surface 4 and adjacent layers. The luminescence from the sensor surface is lead to the detector 6 by an optical fiber 63. The sensor surface 4 and the other layers may be made as small as the diameter of the fiber, creating a very small detector able to measure in narrow places where a camera or even a fiber bundle would never fit.

Figure 4:
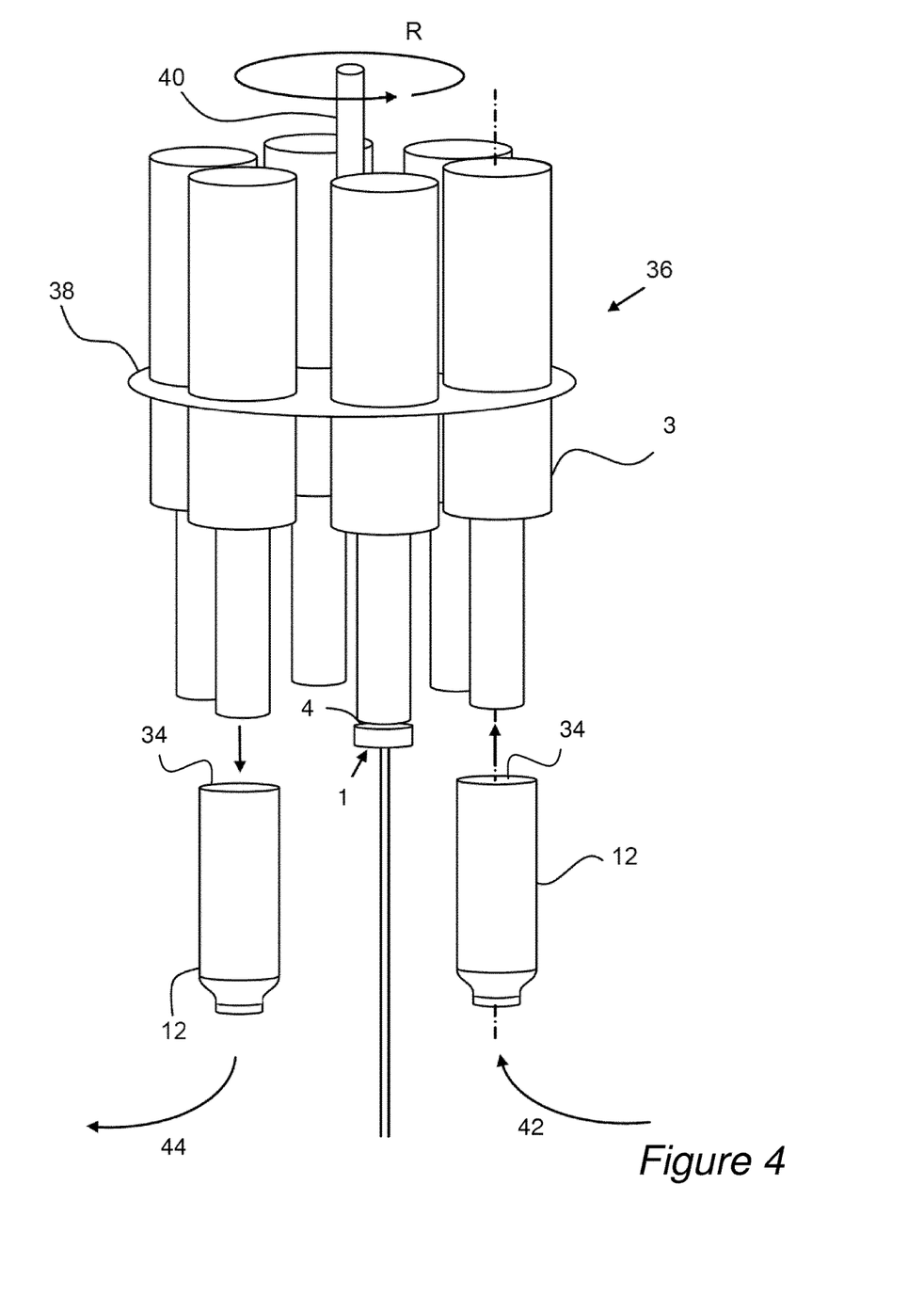
FIG. 4 shows a perspective view a packaging machine where the sensor assembly according to the invention is used online.

FIG. 4 shows a further embodiment of the invention. The figures show an irradiation device 36 in which several above described electron beam emitters 3 are arranged. In this embodiment six emitters 3 are provided to a rotatable carrier 38. The rotatable carrier 38 is, in this embodiment, shaped as a wheel and is rotatable round a centre shaft 40. The direction of the rotation is illustrated by the arrow R and the rotatable movement is continuous. The emitters 3 are fixed to the carrier 38 so that they are being carried along when the carrier 38 rotates. The transportation of the packaging containers is made in a direction transversely to the longitudinal extension of the emitters 3.

The irradiation device 36 further comprises packaging container conveying means, not shown, being adapted to convey the packaging container 10 from an infeed position 42 to an outfeed position 44 synchronously with the carrier revolution movement and in alignment with the electron beam emitter 3. The packaging container 12 is moved synchronously with the electron beam emitter 3 and a longitudinal centre axis of the packaging container 12 is aligned with a longitudinal centre axis of the electron beam emitter 3, see the dashed-dotted line in FIG. 4.

The packaging container conveying means is being further adapted to vertically displace the packaging container 12 in relation to the electron beam emitter 3. In the embodiment shown the electron beam emitter 3 is arranged stationary in the carrier 38 and cannot move towards the packaging container 12. The packaging container conveying means can displace the packaging container 12 between a non-engaged position in which the packaging container 12 and the electron beam emitter 3 are not engaged with each other and a engaged position in which the packaging container 12 and the electron beam emitter 3 are fully engaged with each other. At the infeed and outfeed positions 42, 44 the packaging container 12 is positioned in the non-engaged position, i.e. not in engagement with the electron beam emitter 3.

At the infeed position 42 the packaging containers 12 are supplied to the irradiation device 36. Each packaging container 12 is aligned with a corresponding electron beam emitter 3. When the carrier 38 rotates, so that the electron beam emitter 3 and packaging container 12 rotates from the infeed position 42 to the outfeed position 44, the packaging container 12 conveying means displaces the packaging container 12 towards the electron beam emitter 3 so that the electron beam emitter 3 is received in the opening 34 of the packaging container 12 for sterilizing the packaging container 10. Somewhere between the infeed and outfeed positions 42, 44 the packaging container 12 has been displaced such that the packaging container 12 is fully engaged with the electron beam emitter 3.

The packaging container conveying means is not the focus of this invention and will therefore not be described in detail. It may be arranged on the carrier 38, or on the electron beam emitters 3, or a combination thereof. It may alternatively be arranged separate from the carrier 38 but able to convey the packaging containers 12 synchronous with the carrier rotation. For example it may be arranged on an irradiation shielding device enclosing the carrier 38. The packaging conveying means is provided with packaging container gripping means that is adapted to grip the packaging container 12.

When reaching the outfeed position 44 a sterilization cycle, or irradiation cycle, of the packaging container 12 is completed and the packaging container 12 has been retracted from the engaged position back to the non-engaged position. Hence, the packaging container 12 is then ready to be fed out from the irradiation device 36 for further transfer to a filling device (not shown). Upon further rotation of the carrier 38, from the outfeed position 44 and back to the infeed position 42, the electron beam emitter 3 is not engaged with any packaging container 12 but is still maintained in operation, i.e. it still emitting the same electron beam. When reaching the infeed position 42 again a new sterilization cycle is commenced with a new packaging container 12 supplied at the infeed position 42.

At the infeed 42 position the packaging container 12 is transferred to the carrier 38 of the irradiation device 36. The infeed (not shown) may be a conveyor of any conventional type, for example a star wheel. At the outfeed position 44 the packaging container 12 is transferred from the carrier 38 to the outfeed (not shown) for further transport to a filling station. Like the infeed (not shown), the outfeed (not shown) may be a conveyor of any conventional type, for example a star wheel.

In the irradiation device 36 of the present invention the sensor device 1 is stationary arranged in the area between the outfeed position 44 and the infeed position 42, i.e. the area in which no packaging containers 12 are present in the irradiation device 36. The sensor device 1 is arranged such that the electron beam emitters 3 can pass over a sensor surface 4, and further it is arranged so that when an electron beam emitter 3 is passed above it the electron exit window 2 is temporarily in line with the sensor device 1 for allowing the sensor device 1 to measure the dose control parameters of the electron beam of said electron beam emitter 3.

When the electron beam emitter 3 is passing the sensor device 1, planes representing the sensor surface 4 and the electron exit window 2 are at least temporarily substantially parallel with each other. Further, the longitudinal axis of the electron beam emitter 3 is aligned with the centre of the sensor surface 4, such that the sensor device 1 can collect information from the entire electron beam 16 being emitted through the plane of the electron exit window 2. A distance d in the range of approximately 0.5-15 mm is formed between the electron exit window 2 and the sensor surface 4. Preferably, a distance d in the range of approximately 1-10 mm is formed between the electron exit window 2 and the sensor surface 4. The distance is measured between the electron exit window foil and the sensor surface 4. Generally, it is true that the smaller the gap, the better the measurement.

The irradiation device 36 has been described in a schematic way. Only parts of the irradiation device 36 being involved in the invention has been described, but it is to be understood that the irradiation device comprises also additional parts such as drive units for driving the carrier 38 and the packaging conveying means, irradiation shielding enclosing the irradiation device 36 for securing that electrons and x-rays are not spread to the environment outside of the device, and aseptic barriers being either flow barriers or physical walls, or a combination of the two, for creating and maintaining satisfactory aseptic zones.

It is understood that other variations in the present invention are contemplated and in some instances, some features of the invention may be employed without a corresponding use of other features. The skilled person understands that the detector or camera 6 could look at the luminescence from the electron excitable material 5 from an angle instead of in line with the electron beam. A mirror could also be used for placing the detector 6 differently. Accordingly, it is appropriate that the appended claims be construed broadly in a manner consistent with the scope of the invention.

The invention claimed is:

1. A sensor assembly for continuous measurement of at least one dose control parameter of an electron beam during a part of the duration of a sterilizing process of package material, said sensor assembly comprising:
   an electron beam emitter configured to emit an electron beam (e–) from an electron exit window; and
   a sensor comprising:
      a sensor surface comprising an electron excitable material arranged to be radiated with at least a part of said electron beam (e–) so as to excite said electron excitable material so that said electron excitable material emits luminescence, wherein said sensor surface is covered by a metal coating facing the electron beam emitter; and
      a detector arranged and configured to detect said luminescence,
   wherein said electron beam emitter is configured to emit a continuous electron beam (e–) during a predetermined time period so as to irradiate and sterilize package material.

2. The sensor assembly according to claim 1, wherein said electron beam emitter is a low voltage electron beam emitter.

3. The sensor assembly according to claim 1, wherein said excitable material is selected from the group consisting of:
   YAG:Ce crystal, YAG:Ce powder, $CaF_2$:Eu, $Gd_2O_2S$:Tb, LuAG:Ce, and YAP:Ce ($Mg_4FGeO_6$:Mn).

4. The sensor assembly according to claim 1, wherein said detector is selected from the group consisting of:
   a CCD-camera, a ICCD-camera, a COMS-camera, a photo multiplier, and a photo diode.

5. The sensor assembly according to claim 1, wherein said metal coating is selected from the group consisting of:
   rhodium, platinum, osmium, iridium, ruthenium, palladium, and gold.

6. The sensor assembly according to claim 1, wherein said metal coating is made of rhodium.

7. The sensor assembly according claim 1, wherein said metal coating is grounded.

8. The sensor assembly according to claim 1, further comprising a glass window arranged in thermal connection with the sensor surface, said glass window facing the detector and being in thermal connection with a heat conductive element.

9. The sensor assembly according to claim 1, further comprising a lead window arranged between the sensor surface and the detector.

10. The sensor assembly according to claim 1, wherein said dose control parameter is dose rate (kGy/s).

11. The sensor assembly according to claim 1, wherein said detector is configured to collect the luminescence from said sensor surface via an optical fiber.

12. The sensor assembly according to claim 1 wherein said sensor:
   is connected to a processor configured to process information from the sensor; and
   is arranged to generate a 1D or 2D image of the dose control parameter of the electron beam.

13. The sensor assembly according to claim 1, wherein planes of the sensor surface and the electron exit window are parallel.

14. The sensor assembly according to claim 13, wherein a longitudinal axis of the electron beam emitter is aligned with a center of the sensor surface.

15. A packaging machine for producing food packages comprising the sensor assembly according to claim 1.

16. The sensor assembly according to claim 1, wherein said emitted luminescence is proportional to an intensity of the electron beam (e–), and wherein said sensor is connected to a processor configured to receive information from the sensor and measure the dose control parameter based on the detected luminescence.

17. A method for continuous measurement of at least one dose control parameter of an electron beam of an electron beam emitter during a part of the duration of a sterilizing process of package material, said method comprising:
   forcing the electrons (e–) of an electron beam to hit a sensor surface, said sensor surface being configured to generate luminescence when hit by the electrons (e–), and said sensor surface covered by a metal coating facing the electron beam emitter; and
   detecting the generated luminescence by at least one detector.

18. The method according to claim 17, wherein said generated luminescence is proportional to an intensity of the electron beam, and wherein the method further comprises measuring the dose control parameter based on the detected luminescence.

19. The method according to claim 17, further comprising generating a 1D or 2D image of the dose control parameter based on the detected luminescence.

20. The method according to claim 17, wherein said a metal coating is made of rhodium.

* * * * *

UNITED STATES PATENT AND TRADEMARK OFFICE
CERTIFICATE OF CORRECTION

PATENT NO.        : 10,279,064 B2
APPLICATION NO.   : 15/527490
DATED             : May 7, 2019
INVENTOR(S)       : Alaa Omrane

Page 1 of 1

It is certified that error appears in the above-identified patent and that said Letters Patent is hereby corrected as shown below:

In the Claims

In Column 9, Line 50, in Claim 7 after "according" insert --to--.

Signed and Sealed this
Twentieth Day of August, 2019

Andrei Iancu
*Director of the United States Patent and Trademark Office*